United States Patent [19]

Garnier

[11] 3,952,870

[45] Apr. 27, 1976

[54] CONTAINER FOR DENTAL INSTRUMENTS

[75] Inventor: Marcel Garnier, Besancon, France

[73] Assignee: Micro-Mega, France

[22] Filed: July 8, 1975

[21] Appl. No.: 593,956

Related U.S. Application Data

[62] Division of Ser. No. 422,190, Dec. 6, 1973, abandoned.

[30] Foreign Application Priority Data

Dec. 19, 1972 France ............................ 72.45279

[52] U.S. Cl. ............................... 206/369; 206/63.5; 206/382; 206/443; 206/451; 206/468; 206/471
[51] Int. Cl.² ......................................... A61C 19/02
[58] Field of Search ................... 206/63.5, 329, 332, 206/328, 334, 341, 368, 369, 379, 382, 443, 451, 462, 468, 471; 229/9, 19; 24/81 BF, 255, 255 TV

[56] References Cited

UNITED STATES PATENTS

| 2,251,609 | 8/1941 | Freeburg ............................ 206/329 |
| 2,628,711 | 2/1953 | Flannery ............................ 206/382 |
| 2,792,111 | 5/1957 | Ringler et al. ...................... 206/329 |
| 2,993,590 | 7/1961 | Denton ............................... 206/462 |
| 3,303,928 | 2/1967 | Meilleur ............................. 206/329 |
| 3,322,268 | 5/1967 | Larkin ................................ 206/329 |
| 3,417,866 | 12/1968 | Omer ................................. 206/329 |
| 3,812,963 | 5/1974 | Zahuranec et al. .................. 206/468 |

FOREIGN PATENTS OR APPLICATIONS 1,225,798  3/1971  United Kingdom ................ 206/490

Primary Examiner—George E. Lowrance
Assistant Examiner—Bruce H. Bernstein
Attorney, Agent, or Firm—Robert E. Burns; Emmanuel J. Lobato; Bruce L. Adams

[57] ABSTRACT

A container for dental instruments has a thin plate provided with a plurality of pairs of opposed recesses disposed in two parallel rows in a major surface of the plate. A plurality of channels connect the two recesses in each of the pairs of recesses. Dental instruments are received by the pairs of recesses and their interconnecting channels and are covered by a cover secured to the surface of the plate having the recesses. A plurality of containers may be stacked and held together by a clamp for ease of shipping or storage.

5 Claims, 2 Drawing Figures

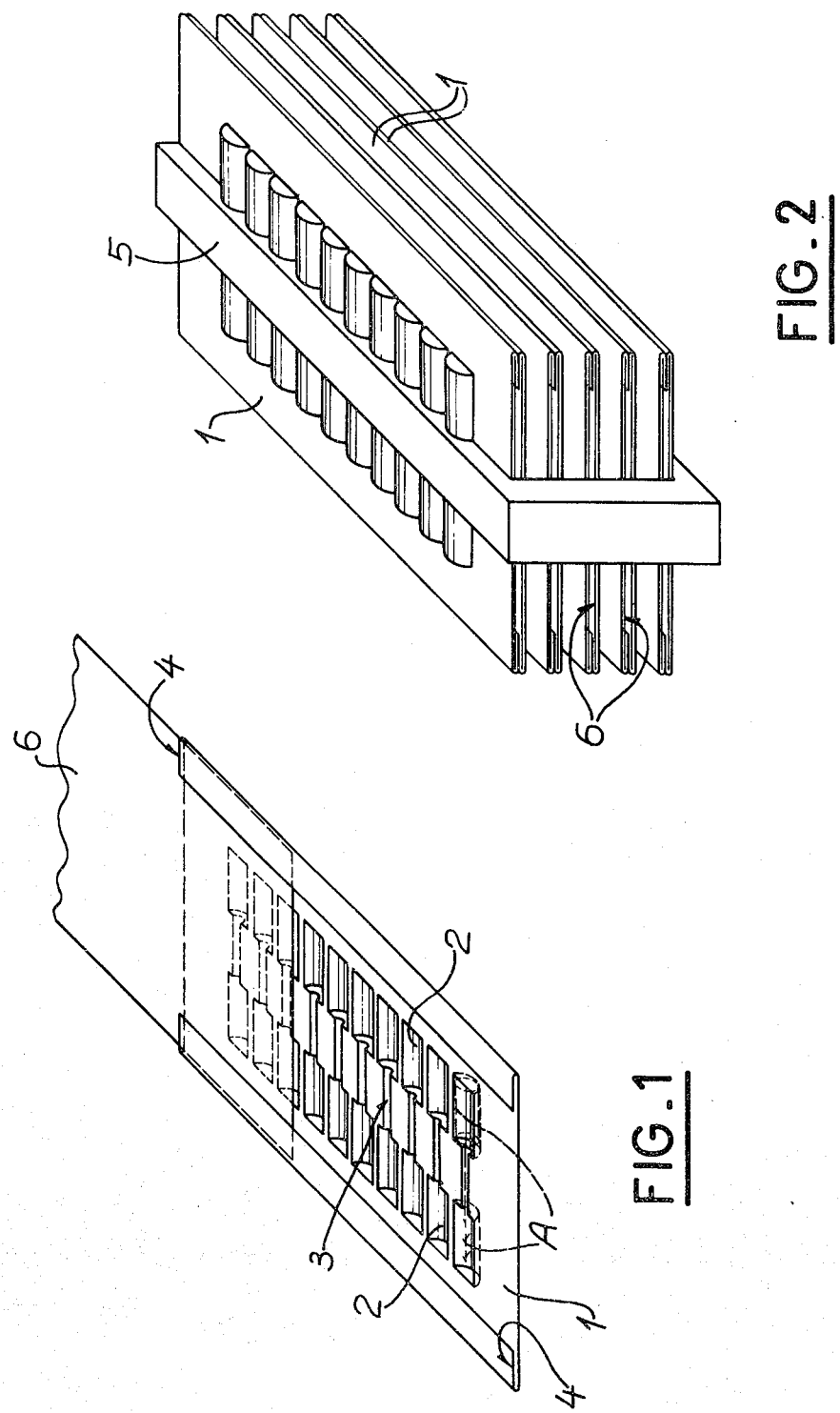

CONTAINER FOR DENTAL INSTRUMENTS

This is a divisional, of application Ser. No. 422,190, filed Dec. 6, 1973, now abandoned.

BACKGROUND OF THE INVENTION

The present invention relates to containers and more particularly to a new and improved container for dental instruments.

Dental instruments used for the treatment of cavities, for instance instruments used for the extraction of nerves, comprise a narrow rod carried by a cylindrical handle having a larger diameter than the rod and sufficient length for gripping the instrument. These instruments are relatively fragile and should be stored and shipped in containers that provide them protection.

SUMMARY OF THE INVENTION

It is a primary object of the invention to provide a container for storing and shipping dental, surgical instruments and the like that will provide them with a high degree of protection.

Another object is to provide a container for dental instruments that can be conveniently stacked with other containers for ease of shipping and storage.

Still another object of the present invention is to provide a container for dental instruments that is inexpensive and easy to manufacture.

A container according to the invention comprises a thin plate having a first and second major surface on opposite sides thereof. The first major surface is provided with a plurality of pairs of opposed recesses disposed in two parallel rows. Each pair of recesses has a channel disposed in the first major surface connecting the two recesses. The second major surface or opposite side surface has a plurality of pairs of opposed bulges protruding therefrom and arranged in two parallel rows. Each of the bulges corresponds to one of the recesses in the first major surface. Portions of the thin plate along each of two opposed longitudinal edges are folded back to the first major surface of the thin plate to define a slot therebetween. A cover is disposed on the first major surface to cover the recesses and protect dental instruments contained therein.

A pair of opposed longitudinal edges of the cover are received by the slots along corresponding longitudinal edges of the thin plate to hold the cover in place. A plurality of containers are stacked and clamped together to facilitate storage and shipping. The containers are stacked in pairs so that the containers in a pair are arranged with their covers facing each other and their second major surfaces facing second major surfaces of the next adjacent pairs of containers. A substantially U-shaped clamp engages the stack of containers with legs of the U-shaped clamp inserted in the space between the opposed parallel rows of bulges of the uppermost and lowermost containers in the stack.

BRIEF DESCRIPTION OF THE DRAWINGS

Other features and advantages of the container for dental instruments according to the invention will be apparent from the disclosure and appended claims and drawings in which:

FIG. 1 is a perspective view of a container according to the invention; and

FIG. 2 is a perspective view of a stack of containers like that shown in FIG. 1.

DESCRIPTION OF THE PREFERRED EMBODIMENT

A container for dental instruments according to the invention illustrated in the drawings comprises a thin plate 1 having a first and second major surface. A plurality of recesses 2, disposed in opposed pairs arranged in two parallel rows, are provided in the first major surface of the thin plate 1. The recesses 2 of each of the pairs of recesses are connected by a channel 3 disposed therebetween.

Each of the pairs of recesses 2 and the corresponding channel 3 are adapted to receive a dental instrument A. These dental instruments have the form of a narrow rod carried by a cylindrical handle. One of the recesses 2 of a pair receives the handle of the instrument while the narrow rod extends through the channel 3 into the other recess 2 of the pair. The end of the narrow rod remote from the handle has means for carrying out some dental treatment; for instance nerve extractions.

Marginal edge portions of sheet 1 along a pair of opposed longitudinal edges, are folded back to the first major surface and define a pair of grooves 4 between the fold and the sheet. A sheet cover 6 has a pair of opposed longitudinal edges received by the grooves 4. The cover 6 covers the recesses 2 to protect dental instruments stored therein and is held in place by the folded portions of sheet 1, or may be removed by sliding it in a longitudinal direction. The grooves 4 need not be provided by bending over portions of the sheet 1, but may be provided in some other manner without departing from the scope of the invention.

The thin plate 1 is made of a suitable material; for example a thermoplastic material. The cover 6 may be made of cardboard, plastic, or some other material.

A plurality of containers may be stacked as illustrated in FIG. 2. The containers are arranged in pairs so that their covers 6 are facing each other, and the pairs of containers are arranged so that the second major surfaces of the plates 1 in next adjacent pairs face each other. The second major surfaces of the plates 1 have a plurality of bulges protruding therefrom where the bulges correspond to the recesses 2 in the first major surfaces and are arranged in parallel rows with a space therebetween. A clamp 5, substantially U-shaped, engages the stack of containers, with one leg of the clamp 5 inserted in the space between the row of bulges on the uppermost container of the stack, and another leg of the clamp inserted in the space between the row of bulges on the lowermost containers of the stack.

What I claim and desire to secure by letters patents is:

1. In combination:
   a. a plurality of containers for dental instruments each having a covered side and an opposite side, said plurality of containers being stacked in pairs having the covered sides of the containers in said pairs opposed to each other, each of said containers comprising a thin plate having a first and second major surface and a pair of opposed longitudinal edges, said first major surface corresponding to the covered side being provided with a plurality of pairs of opposed recesses connected by a channel therebetween disposed in two parallel rows for receiving dental instruments therein, and said second major surface having a plurality of pairs of opposed bulges disposed in two parallel rows with a space defined therebetween, said bulges corresponding to said recesses in said first major surface, a cover disposed on said first major surface for covering said recesses to protect dental instruments contained therein and to hold them in the container, and means for securing said cover to said thin plate; and b. a substantially U-shaped clamp having two legs engaging said stack of containers with a leg of said clamp inserted in said space between said parallel rows of bulges of an uppermost container of said stack, and another leg of said clamp inserted in said space between said parallel rows of bulges of a lowermost container of said stack.

2. A combination according to claim 1 wherein said means for securing said cover to said first major surface comprises a portion of said thin plate along each of said opposed longitudinal edges reversely folded back to said first major surface a length of said longitudinal edges to define a slot between said folded portions of said thin plate and said first major surface for receiving corresponding longitudinal edges of said cover to hold said cover in place.

3. A combination according to claim 1, wherein said thin plate is made of thermoform plastic.

4. A combination according to claim 1, wherein said cover is a substantially flat sheet.

5. A combination according to claim 1, wherein said pairs of opposed bulges are disposed in said plate of each of said plurality of containers relative to the edges of said plate to allow stacking of the respective plates, having a plurality of pairs of opposed bulges similarly disposed in two parallel rows, so that the bulges of one of said plates are between the bulges of another of said plates and the edges of said plates are in registry.

* * * * *